United States Patent [19]

Kirchmeyer et al.

[11] Patent Number: 5,426,205

[45] Date of Patent: Jun. 20, 1995

[54] PERFLUOROALKYLSULPHONAMIDOALK-OXYSILANES

[75] Inventors: Stephan Kirchmeyer, Leverkusen; Martin Richter, Langenfeld, both of Germany

[73] Assignee: Bayer Aktiengesellschaft, Leverkusen, Germany

[21] Appl. No.: 296,310

[22] Filed: Aug. 25, 1994

[30] Foreign Application Priority Data

Aug. 31, 1993 [DE] Germany ............... 43 29 262.3

[51] Int. Cl.⁶ .................................... C07F 7/10
[52] U.S. Cl. ........................................ 556/422
[58] Field of Search ............................ 556/422

[56] References Cited

U.S. PATENT DOCUMENTS

| | | |
|---|---|---|
| 2,803,656 | 8/1957 | Ahlbrecht et al. . |
| 3,787,467 | 1/1974 | Lucking et al. ............ 556/422 |
| 3,803,199 | 4/1974 | Voss et al. ............... 556/422 |
| 4,265,831 | 5/1981 | Mitschke et al. . |

FOREIGN PATENT DOCUMENTS

| | | |
|---|---|---|
| 0007519 | of 1984 | European Pat. Off. . |
| 0125826 | 11/1984 | European Pat. Off. . |
| 2203858 | 5/1974 | France . |
| 2307377 | of 1974 | Germany . |
| 2218097 | 11/1989 | United Kingdom . |

*Primary Examiner*—Paul F. Shaver
*Attorney, Agent, or Firm*—Sprung Horn Kramer & Woods

[57] ABSTRACT

Novel perfluoroalkylsulphonamidoalkoxysilanes suitable as hydrophobing and oleophobing agents for textiles and stone materials of the formula

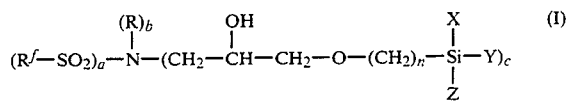

wherein $R^f$ represents a monovalent perfluoroalkyl group with 4 to 20 carbon atoms, R represents a monovalent organic group which is inert towards isocyanate groups at temperatures below 100° C., X, Y and Z represent identical or different organic groups which are inert towards isocyanate groups at temperatures below 100° C., with the proviso that at least one of these groups is an alkoxy group, a is 1 or 2, b is 0 or 1, c is 3-a-b, but at least 1, and n is an integer from 2 to 4, and a process for their preparation.

4 Claims, No Drawings

PERFLUOROALKYLSULPHONAMIDOALKOXYSILANES

The present invention relates to alkoxysilane compounds which contain fluorine atoms, a process for their preparation and their use as conditioning, protective and impregnating agents for stone materials, textile materials and paper.

Compounds with perfluoroalkane groups have a pronounced effect with respect to repelling water and dirt, due to their surface tension. DE-A 39 13 485 describes sulphonamidoalkoxysilanes which contain fluorine as water and oil repellent compounds. The synthesis of this type of compound, however, is complicated and not very suitable for industrial implementation. In one example, for instance, in a multi-stage reaction perfluroalkylsulphonamide is reacted with allyl bromide, then hydrosilylated with trichlorosilane and finally reacted with alcohol to give the perfluoroalkylsulphonamidoalkoxysilane.

The object of the invention is to provide new types of fluorine-containing alkoxysilane compounds which are simple to prepare and are suitable as water, oil and dirt repellent materials.

Surprisingly it has now been found that compounds of the following general formula (I) can be prepared in high yield by reacting perfluorosulphonamides with glycidyl silanes in a single-stage reaction. This is surprising and could not be predicted by a person skilled in the art because, according to specialist opinion, sulphonamides should not react with glycidyl compounds due to the low nucleophilicity of the sulphonamide group.

Furthermore, compounds of the general formula (I) are suitable as a conditioning, protective and impregnating agents for stone materials, textile materials and paper.

The invention therefore provides silane compounds which contain fluorine atoms, of the general formula (I)

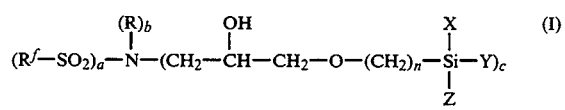

wherein
R$^f$ represents a monovalent perfluoroalkyl group with 4 to 20 carbon atoms,
R represents a monovalent organic group which is inert towards isocyanate groups at temperatures below 100° C.,
X,Y and Z represent identical or different organic groups which are inert towards isocyanate groups at temperatures below 100° C., with the proviso that at least one of these groups is an alkoxy group,
a is 1 or 2,
b is 0 or 1,
c is 3-a-b, but at least 1, and
n is an integer from 2 to 4.

The invention also provides a process for preparing compounds of the general formula (I), characterized in that 1 mole of a compound of the general formula (II)

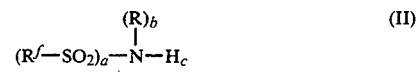

wherein
R$^f$ represents a monovalent perfluoroalkyl group with 4 to 20 carbon atoms,
R represents a monovalent organic group which is inert towards isocyanate groups at temperatures below 100° C.,
a is 1 or 2,
b is 0 or 1, and
c is 3-a-b, but at least 1,
reacts with c moles of a compound of the general formula (III) at temperatures from −20° to 200° C.

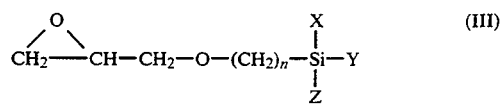

wherein
X,Y and Z represent identical or different organic groups which are inert towards isocyanate groups at temperatures below 100° C., with the proviso that at least one of these groups is an alkoxy group, and
n is an integer from 2 to 4.

Finally, the invention provides use of compounds of the general formula (I) as conditioning, protective and impregnating agents for stone materials, textile materials and paper.

The group R$^f$ is a monovalent perfluoroalkyl group with 4 to 20 carbon atoms, e.g. straight-chain or branched perfluorobutane, perfluoropentane, perfluorohexane, perfluoroheptane, perfluorooctane, perfluorononane, perfluorodecane or perfluorododecane groups, preferably perfluorobutane or perfluorooctane groups. Group R is a monovalent organic group which is inert towards isocyanate groups at temperatures below 100° C., preferably a monovalent aliphatic group with 1 to 4 carbon atoms, e.g. a methyl, ethyl, propyl, butyl or 1-methylethyl group, preferably a methyl or ethyl group.

The organic groups X, Y and Z can be identical or different and are inert towards isocyanate at temperatures below 100° C. Preferably X, Y and Z are monovalent alkoxy groups, optionally interrupted by one or two oxygen atoms, with 1 to 6 carbon atoms such as e.g. methoxy, ethoxy, propoxy, butoxy or methoxyethoxy groups, cycloalkoxy groups with 6 to 10 carbon atoms such as e.g. cyclohexyloxy groups, aryloxy groups with 6 to 10 carbon atoms such as e.g. phenoxy groups, alkyl groups with 1 to 6 carbon atoms such as e.g. methyl, ethyl, propyl or butyl groups, cycloalkyl groups with 6 to 10 carbon atoms such as e.g. cyclopentyl, cyclohexyl or methylcyclohexyl groups, or optionally substituted aryl groups with 6 to 10 carbon atoms such as e.g. phenyl or tolyl groups. It is important that at least one of the groups X, Y or Z is an alkoxy group.

The alkoxysilane compounds which contain fluorine atoms of the general formula (I) according to the invention preferably possess just one perfluoroalkyl group R$^f$ and one alkyl group R. It is also possible, however, to react bis-(perfluoroalkylsulphonyl)-imides or unsubstituted perfluoroalkylsulphonamides, wherein bis-(perfluoroalkylsulphonyl)-imidoalkoxysilanes and perfluoroalkylsulphonamidobisalkoxysilanes respectively are obtained.

Perfluoroalkylsulphonamideoalkoxysilanes according to the invention can be prepared by reacting 1 mole of a compound of the general formula (II)

wherein
- $R^f$ represents a monovalent perfluoroalkyl group with 4 to 20 carbon atoms,
- R represents a monovalent organic group which is inert towards isocyanate groups at temperatures below 100° C., and
- a is 1 or 2,
- b is 0 or 1, and
- c is 3-a-b, but at least 1, with c moles of a compound of the general formula (III),

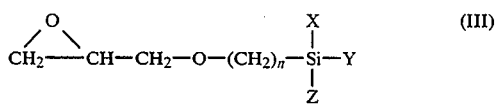

wherein
X,Y and Z represent identical or different organic groups which are inert towards isocyanate groups at temperatures below 100° C., with the proviso that at least one of these groups is an alkoxy group, and
n is an integer from 2 to 4,
at temperatures of −20° to 200° C., preferably between 60° and 150° C., in particular between 80° and 120° C. The molar ratio 1:c depends on the chemical nature of the starting compounds (II) and is 1:1 for N-alkylperfluoro-alkylsulphonamides and bis-(perfluoroalkylsulphon)-imides and 1:2 for unsubstituted perfluoroalkylsulphonamides. The sulphonamides or sulphonimides (II) react with the glycidyl compound (III) in a ting-opening nucleophilic substitution reaction, wherein the attack is virtually exclusively at the 1-carbon atom in the glycidyl group. The reaction can, however, also lead to small amounts of a product which is produced by attack of the sulphonamide or sulphonimide at the 2-carbon atom in the glycidyl group.

Suitable starting compounds of the general formula (II) are perfluoroalkylsulphonamides such as e.g. N-methyl-1 -perfluorobutanesulphonamide, N-ethyl-1-perfluorobutane-sulphonamide, N-propyl-1-perfluorobutanesulphonamide, N-propyl-1-perfluoropentanesulphonamide, N-ethyl-1-perfluoropentanesulphonamide, N-methyl-1-perfluoro-hexanesulphonamide, N-ethyl-1-perfluorohexanesulphonamide, N-propyl-1 -perfluorohexanesulphonamide, N-methyl-1-perfluoro-heptanesulphonamide, N-ethyl-1-perfluoroheptanesulphonamide, N-butyl-1-perfluoroheptanesulphonamide, N-methyl-1-perfluorooctanesulphonamide, N-ethyl-1-perflorooctanesulphonamide, N-1-methylethyl-1-perfluorooctanesulphonamide, N-butyl-1-perfluoroocanesulphonamide, N-ethyl-1-perfluorononanesulponamide, N-propyl-1-perfluorodecane-sulphonamide and N-propyl-1-perfluorododecanesulphonamide, perfluorobutanesulphonamide, perfluorohexanesulphonamide and perfluorooctanesulphonamide and bis-(perfluoroalkylsulphonyl)-imides such as bis(perfluorobutylsulphon)-imide, bis-(perfluorohexyl-sulphon)-imide and bis-(perfluorooctylsulphon)-imide. Preferred glycidylsilanes are 3-glycidyl-propyltrimethoxysilane and 3-glycidylpropyltri(methoxyethoxy)silane.

The reaction step can be checked by means of the decrease in the epoxide bands at ca. 910 cm$^{-1}$ and the N-H bands at ca. 3170 cm$^{-1}$ in the infrared spectrum. After complete reaction of the starting materials both bands have virtually vanished and new bands for the hydroxyl vibration appear at ca. 3400 to 3500 cm$^{-1}$. The reaction proceeds spontaneously without further action after mixing the reaction partners. The reaction is performed preferably with the exclusion of moisture, e.g. under an atmosphere of nitrogen. The reaction is preferably performed without adding solvents, but it is also possible to add inert solvents, such as acetone, tetrahydrofuran, methyl-tert.butyl ether, toluene, chloroform or dichloromethane, during reaction. It is also possible to add agents which increase the rate of reaction, such as e.g. quaternary ammonium salts, during reaction. Working under atmospheric pressure is preferred, but elevated pressures may also be used. Otherwise, the process does not require any special features with regard to process engineering. The same is true of working up. After removing the low-boiling fraction (e.g. by distillation or thin layer techniques) the product yields as a water-clear or pale yellow liquid with a purity of more than 95% and can be used according to the invention.

In a special variant, N-alkyl-perfluoroalkylsulphonamide isomers, such as are produced during industrial preparation by electrofluorination and subsequent reaction with alkylamines, mutually react with the glycidylalkoxysilane. The mixture of N-alkyl-perfluoroalkylsulphonamido-alkoxysilanes thereby obtained can be used in the same way as pure compounds of the general formula (I) as conditioning, protective and impregnating agents for stone materials, textile materials and paper.

EXAMPLES

Example 1

51.30 g (0.1 mole) of N-methylperfluorooctylsulphonamide (molar ratio of n-isomer to iso-isomer ca. 80:20) and 36.80 g (0.1 mole) of 3-glycidylpropyltri(methoxyethoxy)silane are heated at 100° C. for 24 hours in a 500 ml three-necked flask fitted with an internal thermometer, nitrogen inlet and mechanical stirrer, under an atmosphere of nitrogen and with the exclusion of moisture. At the end of this time the bands at 912 cm$^{-1}$ and 3170 cm$^{-1}$ in the infrared spectrum have disappeared. The infrared spectrum does not alter any more with further heating. A mixture of the isomers of 3-(N-methyl-N-perfluorooctylsulphonamido)-2-hydroxypropoxy-propyl-tri(methoxyethoxy)silane is produced as a pale yellow viscous liquid.

Example 2

51.3 g (0.1 mole) of N-methylperfluorooctylsulphonamide (molar ratio of n-isomer to iso-isomer ca. 80:20) and 23.60 g (0.1 mole) of 3-glycidylpropyltrimethoxysilane react together in the same way as described in Example 1. A mixture of isomers of 3-(N-methyl-N-perfluorooctyl-sulphonamido)-2-hydroxypropoxypropyl-trimethoxysilane is produced as a pale yellow viscous liquid.

Example 3

31.30 g (0.1 mole) of N-methylperfluorobutylsulphonamide (molar ratio of n-isomer to iso-isomer ca. 95:5) and 23.60 g (0.1 mole) of 3-glycidylpropyltrimethoxysilane react together in the same way as described in Example 1.

A mixture of isomers of 3-(N-methyl-N-perfluorobutyl-sulphonamido)-2-hydroxypropoxy-propyl-trimethoxysilane is produced as a pale yellow viscous liquid.

Example 4

31.30 g (0.1 mole) of N-methylperfluorobutylsulphonamide (molar ratio of n-isomer to iso-isomer ca. 95:5) and 36.80 g (0.1 mole) of 3-glycidylpropyltri(methoxyethoxy)-silane react together in the same way as described in Example 1. A mixture of isomers of 3-(N-methyl-N-perfluorobutyl-sulphonamido)-2-hydroxypropoxypropyl-tri(methoxyethoxy)-silane is produced as a pale yellow viscous liquid.

Example 5 (application example)

Samples of conventional sandy limestone (dimensions 60 mm×40 mm×10 mm) are stored for 5 days at 50° C. and, after cooling are immersed for 30 seconds, in a 30 wt. % strength solution of the fluoroalkoxysilane from Example 1 in butyl acetate. The samples are stored for 7 days at room temperature and for 24 hours at 50° C. The water absorption is then determined after storing in water for 24 hours. The samples absorb on average 1.8 wt. % of water. In comparison with this, untreated samples absorb 10.5 wt. % of water in 24 hours.

Example 6 (application example)

Cotton fabric is immersed for 30 seconds in a 5 wt. % strength solution of the fluoroalkoxysilane from Example 1 in butyl acetate and conditioned for 5 days at room temperature. One drop each of paraffin oil and water are placed on the cotton fabric. Neither drop wets the fabric (contact angle greater than 90° C.). On comparison with this, paraffin oil and water both immediately wet untreated cotton fabric and soak in.

It is understood that the specification and examples are illustrative but not limitative of the present invention and that other embodiments within the spirit and scope of the invention will suggest themselves to those skilled in the art.

We claim:

1. A fluorine-containing silane of the formula

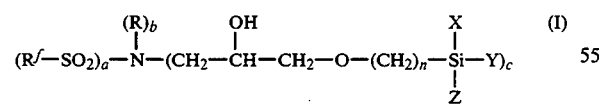

wherein $R^f$ represents a monovalent perfluoroalkyl group with 4 to 20 carbon atoms, R represents a monovalent organic group which is inert towards isocyanate groups at temperatures below 100° C., X, Y and Z represent identical or different organic groups which are inert towards isocyanate groups at temperatures below 100° C., with the proviso that at leat one of these groups is an alkoxy group, a is 1 or 2, b is 0 or 1, c is 3-a-b, but at least 1, and n is an integer between 2 and 4.

2. A compound according to claim 1, wherein

R represents a monovalent aliphatic group with 1 to 4 carbon atoms,

X, Y and Z represent identical or different monovalent alkoxy groups, optionally interrupted by one or two oxygen atoms, with 1 to 6 carbon atoms, cycloalkoxy groups with 6 to 10 carbon atoms, an aryloxy group with 6 to 10 carbon atoms, alkyl groups with 1 to 6 carbon atoms, cycloalkyl groups with 6 to 10 carbon atoms or optionally substituted aryl groups with 6 to 10 carbon atoms, with the proviso that at least one of these groups is an alkoxy group, a is 1, b is 1, c is 1, and n is 3.

3. A process for preparing a compound according to claim 1, comprising reacting 1 molar amount of a compound of the formula

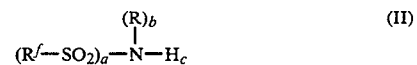

with a c molar amounts of a compound of the formula

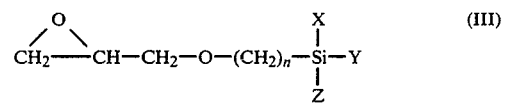

at a temperature from −20° to 200° C.

4. A process according to claim 3, wherein a is 1, b is 1,

X, Y and Z represent identical or different, monovalent alkoxy groups, optionally interrupted by one or two oxygen atoms, with 1 to 6 carbon atoms, cycloalkoxy groups with 6 to 10 carbon atoms, an aryloxy group with 6 to 10 carbon atoms, alkyl groups with 1 to 6 carbon atoms, cycloalkyl groups with 6 to 10 carbon atoms or optionally substituted aryl groups with 6 to 10 carbon atoms, with the proviso that at least one of these groups is an alkoxy group c is 1 and n is 3.

* * * * *